(12) United States Patent
Smith

(10) Patent No.: US 6,238,692 B1
(45) Date of Patent: May 29, 2001

(54) MEDICAL DRESSING FOR APPLICATION AND MAINTENANCE OF MEDICATION ON BODY TISSUE

(76) Inventor: Stephen Jay Smith, 2211 So. Yosemite Cir., Denver, CO (US) 80231

( * ) Notice: Subject to any disclaimer, the term of this patent is extended or adjusted under 35 U.S.C. 154(b) by 1 day.

(21) Appl. No.: 08/880,213

(22) Filed: Dec. 10, 1998

Related U.S. Application Data

(62) Division of application No. 08/556,570, filed on Nov. 13, 1995, now Pat. No. 5,762,955, which is a continuation of application No. 08/191,632, filed on Feb. 4, 1994, now abandoned.

(51) Int. Cl.$^7$ ..................................................... A61F 13/02
(52) U.S. Cl. ........................... 424/448; 424/443; 424/447
(58) Field of Search ................................... 424/443, 447, 424/448

(56) References Cited

U.S. PATENT DOCUMENTS

| 5,271,943 | * | 12/1993 | Bogart et al. | 424/484 |
| 5,462,536 | * | 10/1995 | Braatz et al. | 604/304 |
| 5,534,561 | * | 7/1996 | Volke | 523/111 |
| 5,651,982 | * | 7/1997 | Marx | 424/450 |
| 5,804,213 | * | 9/1998 | Rolf | 424/445 |

* cited by examiner

*Primary Examiner*—Helen L. Pezzuto
(74) *Attorney, Agent, or Firm*—Ramon L. Pizarro

(57) ABSTRACT

A medical method and dressing for application and maintenance of medication on healthy, damaged diseased or infected living tissue. Medication is applied to body tissue and then coated with a bioadhesive providing medication maintenance on tissue and protection from body and other liquids or abrasion thereby preventing removal of the medication during a healing or treatment process.

10 Claims, 1 Drawing Sheet

MEDICAL DRESSING FOR APPLICATION AND MAINTENANCE OF MEDICATION ON BODY TISSUE

This application is a divisional of application Ser. No. 08/556,570 filed Nov. 30, 1995, now U.S. Pat. No. 5,762,955, which is a continuation of Ser. No. 08/191,162, now abandoned.

BACKGROUND OF THE INVENTION

1. Field of the Invention

The present invention relates generally to applying a medication to healthy, damaged, diseased, or infected living tissue and coating the medication with a bioadhesive as a method of maintaining the medication and protecting tissue during a healing and medicating process.

2. Description of the Prior Art

It is well known that many types of medication may be applied to healthy, damaged, diseased, or infected living tissue to assist a healing process, prevent additional harm and infection, and relieve pain or suffering. This has been accomplished by a variety of methods. Depending upon the physiological problem and the type of medication, medication may be injected into the blood stream, taken orally, transferred into the body through healthy tissue or applied directly to the damaged, diseased or infected tissue. In clinical practice there are problems when applying medication directly to healthy, damaged, infected or diseased tissue.

After applying the medication to the tissue area, there is a medical need to maintain the presence of the medication during the healing process, to prevent foreign matter from entering or affecting the tissue, and to protect the injured area from mechanical interference. Presently this need is accomplished by a number of methods such as bandages, physical restraints, and continual maintenance by cleaning, medication administration and re-bandaging. All these devices and techniques may cause discomfort, expense, time, and may result in inefficient healing.

There is also a medical need to apply and maintain medication on healthy tissue for absorption into the body. This type of application involves using a medical device for transdermal delivery (U.S. Pat. No. 4,645,502) or fabric backed dressings that also need maintenance and replacement.

Bioadhesives have been used in surgical methods, dental methods, tissue bonding and applying bandages. U.S. Pat. No. 3,223,083 was an early disclosure of a method for securing bones and skin using bioadhesives. The bioadhesives have also been used to bond bandages, sutures, (U.S. Pat. No. 5,254,132) porous materials (U.S. Pat. No. 4,906,240) or flexible materials (U.S. Pat. No. 4,900,303) to tissues for medical purposes. These bioadhesive techniques involve adhesion of healthy tissue to cellular, plastic, porous, or fabric materials that protect, dispense medication, or sutures closing damaged or diseased tissue. However, the use of these bioadhesives employing auxiliary devices may interfere with the healing process and make clinical processes more difficult.

In actual clinical situations the above techniques and methods may be complex or simply ineffective. Such clinical situations may relate to areas of the body where reliable, simple, predictable, effective retention of medication is extremely difficult or impossible, i.e. wet tissues, limited access, restricted visibility and lighting, mechanical interference (occlusion of teeth -orally, areas of excessive mobility, etc.)

In oral applications, liquids and mechanical interference by tongue, teeth, and cheeks retard the healing process. Saliva may dilute or wash away the medication. Currently, a dental paste mixed with hydrocortisone, called Orabase® by Colgate-Hoyt/Gel-Kam requires application after each meal. A similar dental paste, Kenalog® by Westwood Squibb, needs re-application every 12 hours.

There are many other anatomical regions where internal or external fluids may interfere with the application and retention of medication on injured tissue.

The present invention has solved the problems described above that are common in medical and dental practice.

SUMMARY OF THE INVENTION

The present invention relates to applying a medication to healthy, damaged, diseased, or infected tissue including burns, wounds, pathological lesions, pre-cancerous infections, dermatitis, and surgical incisions and then coating a bioadhesive over the medication. The bioadhesive coating maintains the presence of the medication on the injured tissue, seals the injury, and protects the medication and tissue from possible contamination, dilution, and mechanical interference that may cause additional tissue injury. The adhesive coating provides a means to maintain the medication throughout the healing process of damaged, infected or diseased tissue. The bioadhesives may be applied over various medications such as in intra-oral environments where body fluids or areas of excessive mobility easily removes topical medication, rendering medication ineffective. Other body regions where fluids may remove medication include intra-abdominal, intra-anal, and other regions where circumstances make adhesion of medication difficult or impossible.

The bioadhesive may be coated over medication that has been applied to all internal and external parts of a tissue wound or gash prior to closing the wound. The wound is then pressure closed, sealing the wound and medication on the injured tissue. If the medication is applied to healthy tissue for transdermal delivery, the bioadhesive applied over this medication maintains the medication on the tissue throughout the delivery process in an identical manner as on injured tissue.

Application of the bioadhesive on the medication may be accomplished by wiping using sterile gloves, applying with appropriate devices, spray, painting, or other means to produce a continuous adhesive film on the medicated tissue.

If additional support for damaged, diseased, or infected body sections is required, bandages, splints, other medication dispensing devices, prosthetic devices or any other devices may be applied in conjunction with the inventive process.

For some applications, selected medication may be combined with the proper adhesives prior to application to provide a single step process where conditions and tissue locations make the two step application process difficult.

Accordingly, the object of the invention is to provide a method for maintaining medication on damaged, diseased or infected tissue during the healing process.

Another object of the invention is to provide clinical practitioners when working in clinical situations with a means of using a reliable, simple, predictable, and effective method for retention of medication on damaged, diseased, or infected tissue.

Another object of the invention is to provide a method for maintaining a continuous medication presence on tissue exposed to fluids during the healing process.

Another object of the invention is to provide a method for maintaining continuous medication on healthy tissue for transdermal delivery.

Another object of the invention is to provide a method for maintaining continuous medication on tissue in combination with prosthetic devices, sutures, or mechanical devices used to attach severed digits or limbs, such avulsed teeth, eyeballs, or toenails.

Another object of the invention is to provide a method for applying a combination mixture of a bioadhesive and a medication on or in anatomical regions where access makes the application of separate medication and bioadhesive difficult.

DETAILED DESCRIPTION OF PREFERRED EMBODIMENTS

The present invention relates to the treatment of healthy, damaged, diseased, or infected biological tissue by applying a bioadhesive coating in conjunction with a medication. External biological body tissue may be affected by many harmful afflictions including but not limited to various bruises, burns, dermatologic afflictions, infections, gashes, wounds, herpes sores, canker sores, or intra-oral lesions and skin cancers, such as leukoplakia. Internal body tissues may also be affected by diseases, infections, and injuries and thus require biological medication. For example, intra-abdominal, intra-anal, and intra-oral, intra-vascular, intra-ocular and any other regions where circumstances require application of medication.

Figure 1:
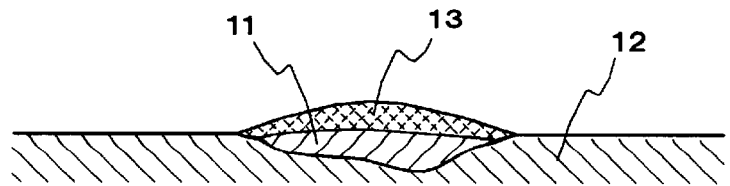
FIG. 1 shows sectional view of a topical tissue coating.

FIG. 1 indicates the process for treatment of surface afflictions. The afflicted tissue and surrounding area is thoroughly cleaned and disinfected using normally accepted methods including but not limited to anti-bacterial soaps. Medication 11 is applied to the injured or affected surface 12 by normal methods including swabbing, flowing, spraying, wiping or use of special applicators. Sufficient quantity is applied to promote a healing process of the injured or diseased tissue.

Next, the bioadhesive liquid 13 is applied to the surface of the medication for retention and protection purposes. Bioadhesive applications are readily accomplished by normal methods including swabbing, flowing, spraying, wiping or use of special applicators. The quantity of bioadhesive should be sufficient to provide a cover to the medication and thereby seal the surface while attaching to the tissue. The bioadhesive polymerizes and bonds to tissue to form a protective and resilient layer on the medication. The resulting product of the process is a tissue dressing that protects the afflicted tissue and maintains mediation on the tissue during the healing process. The application of medication and bioadhesive on healthy tissue for transdermal medication delivery is identical to the method shown in FIG. 1.

Figure 2:
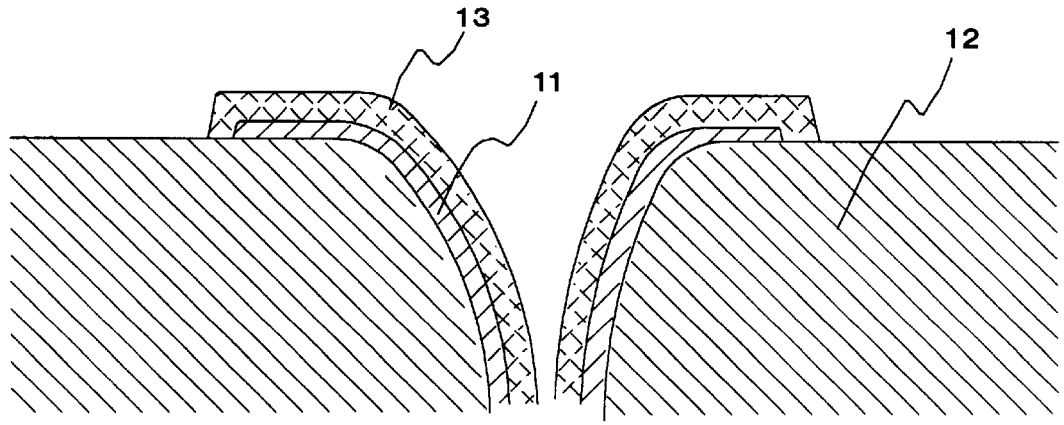
FIG. 2 shows a sectional view of a deep wound with the biological medication and adhesive coating.
Figure 3:
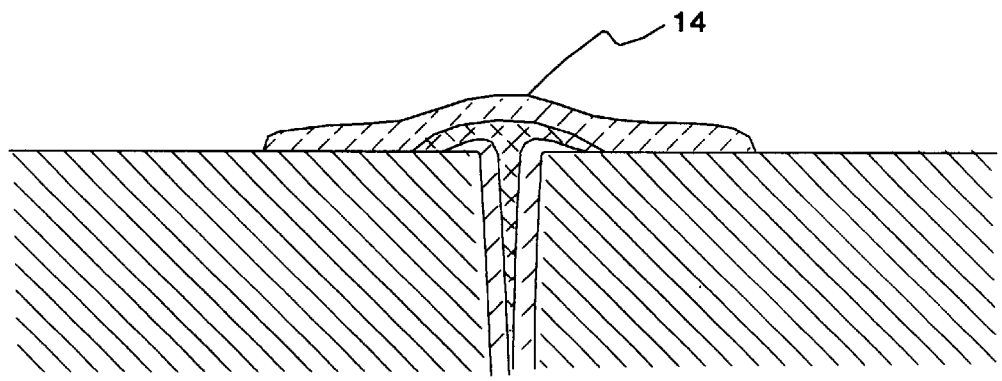
FIG. 3 shows the closure of the FIG. 2 wound and additional topical dressing.

FIG. 2 shows a deep flesh wound receiving the inventive treatment method. The medication 11 is applied internally to all surfaces of the exposed flesh 12 after cleaning and disinfecting all areas. The bioadhesive 13 is then applied to all outer surfaces of the medication, followed by forceful closure of the wound. The closure is physically maintained until the bioadhesive reacts, bonding the internal surfaces together, thereby encapsulating the medication next to the injured surfaces. This bonding time will take less than twenty minutes. This closed wound is depicted in FIG. 3. This same procedure applies to the reattachment of severed body parts such as avulsed teeth, toenails, eyeballs, or severed digits or limbs.

FIG. 3 also indicates an auxiliary exterior bandage, dressing, precast film 14 or sutures that may be used over the inventive method if required for additional external protection.

Figure 4:
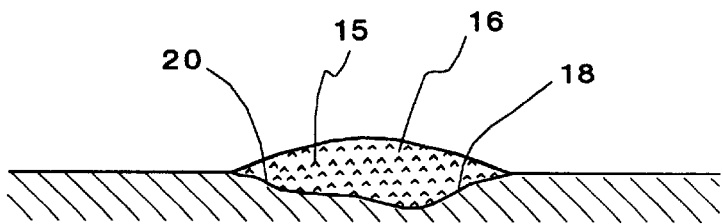
FIG. 4 shows the application of a combination of medication and bioadhesive mixture on injured tissue.

FIG. 4 indicates a method of combining the medication 15 with the bioadhesive 16 prior to applying on cleaned and disinfected living tissue or such as a vertical side 18 of an open wound 20 in inaccessible areas of a body where the individual component applications are not practical. This method combines a medication with a bioadhesive in a 0.1 to 50 weight percent medication of total combination weight. The weight percent depends upon the type of injury, medication and bioadhesives.

The medications used in the inventive method are not critical to this invention and as used herein is meant in the broadest sense as a material that is intended to produce some beneficial effect on the applied tissue or organism. These include but are not limited to corticosteriods, fluorouracil, obtundants, anesthetics, antibiotics, fungicides, anti-inflammatory agents, antibacterial agents, antiseptic agent, and any other medication or combination of medicines used in the process of healing injured or infected tissue, promoting blood clotting or preventing blood clotting, destroying cancer cells, palliative treatments and killing of bacteria or viruses.

Bioadhesives are chemical compounds that have a property or ability to bond to body tissue. There are several kinds of bioadhesives suitable for the invention and the selection depends upon the location of the tissue and the type of medication selected for treating the injury or infection. The bioadhesive chemical groups most useful belong to the cyanoacrylate adhesives, polyurethanes and polypeptide chain adhesives that may be used on wet surfaces. For some cases, the silicones, polyacrylamides, polyisobutylene-mineral oil adhesives, tackified EVA contact adhesives, tackified styrene-isoprene-styrene block copolymers (SIS) may be suitable. For most applications, the bioadhesive should have the property of being biodegradable. Cyanoacrylate adhesives suitable for coating medications include but are not limited to the groups:

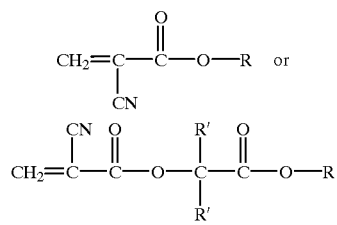

where R is an alkyl or other compound. The R substitute is alkyl of from 10 or 12 or more carbon atoms and preferably n-butyl ($—CH_2—CH_2—CH_2—CH_3$). R' is an individual hydrogen or methyl. These cyanoacrylates are described in U.S. Pat. No. 4,650,826; 4,035,334; 3,995,641; 3,667,472; 3,551,676; and 3,527,224 all of which are incorporated herein in their entirety by reference. Upon application to tissue, the cyanoacrylate compound will polymerize to encapsulate the medication and bond to the tissue. Preferably, thicker viscosity and fast reacting monomers of the cyanoacrylate are desirable.

The polypeptides, described in U.S. Pat. No. 5,197,973, consist of peptide sequences that are capable of forming a-helices in solution.

The urethane adhesives, described in U.S. Pat. No. 5,173,301; 4,994,542; 4,806,614; and 4,740,534, contain at least one NCO terminated hydrophilic urethane prepolymer.

The adhesive selected for the invention should retain the medication in the afflicted area for a period of one to twenty days while healing occurs.

Biological tissues discussed in the invention include human, animal, and vegetable species.

The following example illustrates only some of the many possible uses of the invention and are not intended to limit the scope of the claims in any manner.

EXAMPLE

The present invention was subjected to final clinical test in the most difficult of clinical situations and most primitive conditions in the jungles of Guatemala by treating the Kekchi Indians. Numerous medications were applied and retained by a butyl cyanoacrylate type bioadhesive on large wounds, infections, and lesions, both extra-orally and intra-orally after cleaning and disinfecting the afflicted tissue and surrounding areas. No additional treatment was required for ten days for the lesions and seven to ten days for oral treatments. These were surprising and unexpected long term results necessitated by difficult conditions and numerous patients having little or no access to medical treatment. After thirty days there were no apparent complications or sequelae. All treatments were proven successful.

From the above description of the invention, various changes and modifications in the methods will occur to those skilled in the art. All such modifications coming within the scope of the appended claims are intended to be included therein:

What I claim:

1. A medical dressing in liquid or gel form, the medical dressing being for application against a section of living tissue and being adapted for being shaped in-situ to conform with the section of living tissue being covered with the dressing, the medical dressing comprising:
   a cyanoacrylate adhesive in a liquid or gel state; and
   a medication, the medication being intermixed within the cyanoacrylate adhesive in a ratio of from approximately 0.1 to approximately 50 percent weight of medication weight to total weight of cyanoacrylate adhesive to create a cyanoacrylate adhesive and medication mixture, so that application and in situ curing of the cyanoacrylate adhesive and medication mixture over the living tissue creates a dressing that has assumed the shape of the living tissue covered by the dressing.

2. A dressing according to claim 1 wherein the cyanoacrylate adhesive is of the group:

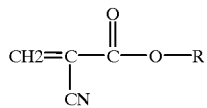

wherein R is another compound containing carbon.

3. A dressing according to claim 2 wherein alkyl is n-octal R is an n-octyl alkyl.

4. A dressing according to claim 1 wherein the cyanoacrylate adhesive is of the group:

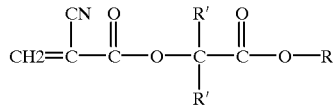

wherein R is an alkyl of from 1 to 12 carbon atoms and R' is an individual hydrogen or methyl.

5. A dressing according to claim 1 wherein said cyanoacrylate adhesive and medication mixture is of a tacky consistency, so that the cyanoacrylate adhesive and medication mixture clings to the living tissue on application of the medication mixture on to a vertical side of an open wound.

6. A mixture in liquid or gel from for creating an in situ medical dressing, the medical dressing being against a section of living tissue, the mixture comprising:
   a cyanoacrylate adhesive in a liquid or gel state; and
   a medication, the medication being intermixed within the cyanoacrylate adhesive in a ratio of from approximately 0.1 to approximately 50 percent weight of medication weight to total weight of cyanoacrylate adhesive to create a cyanoacrylate adhesive and medication mixture, so that application and curing of the cyanoacrylate adhesive and medication mixture on the section of living tissue creates a dressing that has assumed the shape of the living tissue covered by the cyanoacrylate adhesive and medication mixture.

7. A dressing according to claim 6 wherein the cyanoacrylate adhesive is of the group:

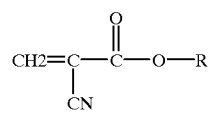

wherein R is a compound containing carbon.

8. A dressing according to claim 7 wherein R is an alkyl of from 1 to 12 carbon atoms.

9. A dressing according to claim 6 wherein the cyanoacrylate adhesive is of the group:

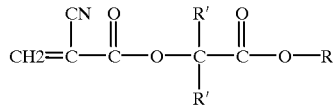

wherein R is an alkyl of from 1 to 12 carbon atoms and R' is and individual hydrogen or methyl.

10. A dressing according to claim 6 wherein said cyanoacrylate adhesive and medication mixture is of a tacky consistency, so that the cyanoacrylate adhesive and medication mixture clings to the living tissue on application of the medication mixture on to a vertical side of an open wound.

* * * * *